United States Patent
Shambaugh, Jr.

(10) Patent No.: US 11,806,049 B1
(45) Date of Patent: Nov. 7, 2023

(54) AUTOMATED AIRWAY OBSTRUCTION CLEARANCE/DROWNING RESCUE DEVICE AND METHOD OF MAKING AND USING THE SAME

(71) Applicant: Charles Shambaugh, Jr., Coral Gables, FL (US)

(72) Inventor: Charles Shambaugh, Jr., Coral Gables, FL (US)

( * ) Notice: Subject to any disclaimer, the term of this patent is extended or adjusted under 35 U.S.C. 154(b) by 0 days.

(21) Appl. No.: 18/211,380

(22) Filed: Jun. 19, 2023

(51) Int. Cl.
*A61B 17/50* (2006.01)
*A61M 1/00* (2006.01)
*A61M 16/20* (2006.01)
*A61M 16/06* (2006.01)

(52) U.S. Cl.
CPC ............... *A61B 17/50* (2013.01); *A61M 1/67* (2021.05); *A61M 16/06* (2013.01); *A61M 16/208* (2013.01)

(58) Field of Classification Search
CPC .......... A61M 16/0003; A61M 16/0006; A61M 16/0009; A61M 16/0072; A61M 16/06; A61M 16/0605; A61M 16/208; A61M 1/67; A61M 1/81; A61M 1/815; A61M 1/94; A61B 17/24; A61B 17/50
See application file for complete search history.

(56) References Cited

U.S. PATENT DOCUMENTS

| | | | |
|---|---|---|---|
| 4,662,367 A | 5/1987 | Gore, Jr. | |
| 4,971,053 A * | 11/1990 | Tarrats | A61B 17/50 128/206.28 |
| 6,986,773 B1 | 1/2006 | Manougian | |
| 8,454,624 B2 | 6/2013 | DeLuca et al. | |
| 2021/0251658 A1* | 8/2021 | Leifenberg | A61B 17/24 |

OTHER PUBLICATIONS https://www.amazon.com/s?k=device+to+stop+choking&gclid=CjwKCAjwov6hBhBsEiwAvrvN6Be3WhL3-kZB40NBxQrGuqQbOBSrHOeO1sBfB3Rp89YoeXz5KHMiRoCmssQAVD_BWE&hvadid=651122440245&hvdev=c&hv ocphy=9024532&hvnetw=g&hvqmt=e&hvrand=11436069016287759862&hvtargid=kwd-838637016845&hydadcr=874_1015116426&tag=googhydr-20&ref=pd_sl_85vzkcggdg_e.
https://www.dechoker.com/.

* cited by examiner

*Primary Examiner* — Joseph D. Boecker
(74) *Attorney, Agent, or Firm* — Ashley D. Johnson; Dogwood Patent and Trademark Law

(57) ABSTRACT

The invention is an aspiration device that can be used to dislodge an object from a choking victim's airway or to remove water from a drowning victim's airway. The device comprises a hollow cylinder comprising a movable piston mounted within the cylinder interior. A system for automatically moving the piston rearwardly to expand the size of the cylinder chamber is provided. An airway extends between the cylinder chamber and a facemask so that air can be drawn into the cylinder chamber through the mask when the piston is moved in a rearward direction. A compressed spring disposed within the cylinder chamber can bias the piston in a rearward direction. A releasable latch that allows the piston to move from a forward position to a released position is housed within an endcap.

18 Claims, 7 Drawing Sheets

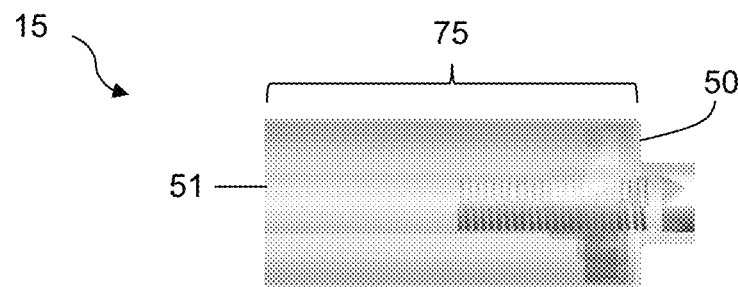
Fig. 3c
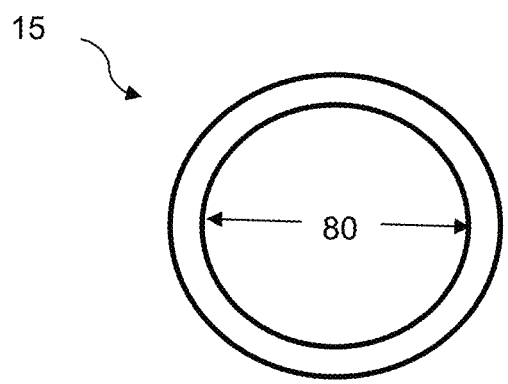
Fig. 3d
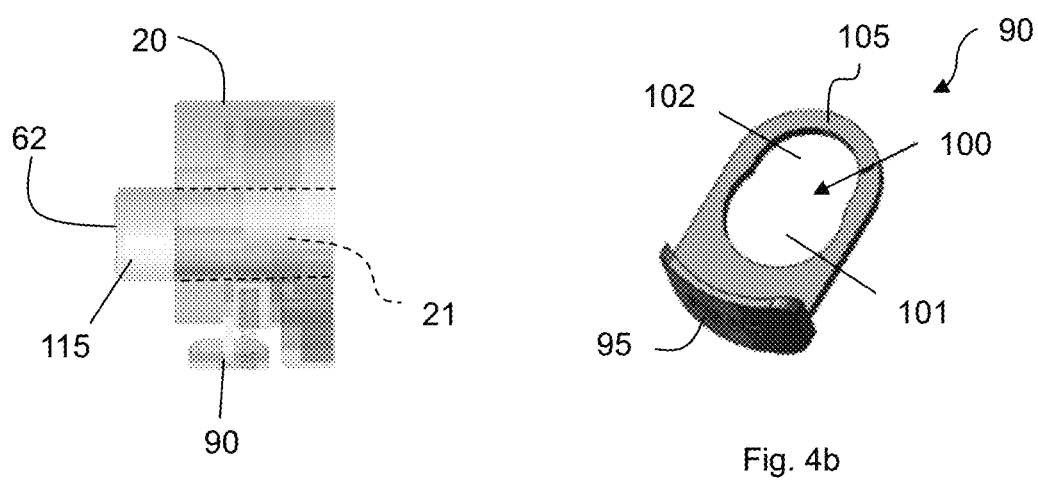
Fig. 4a
Fig. 4b

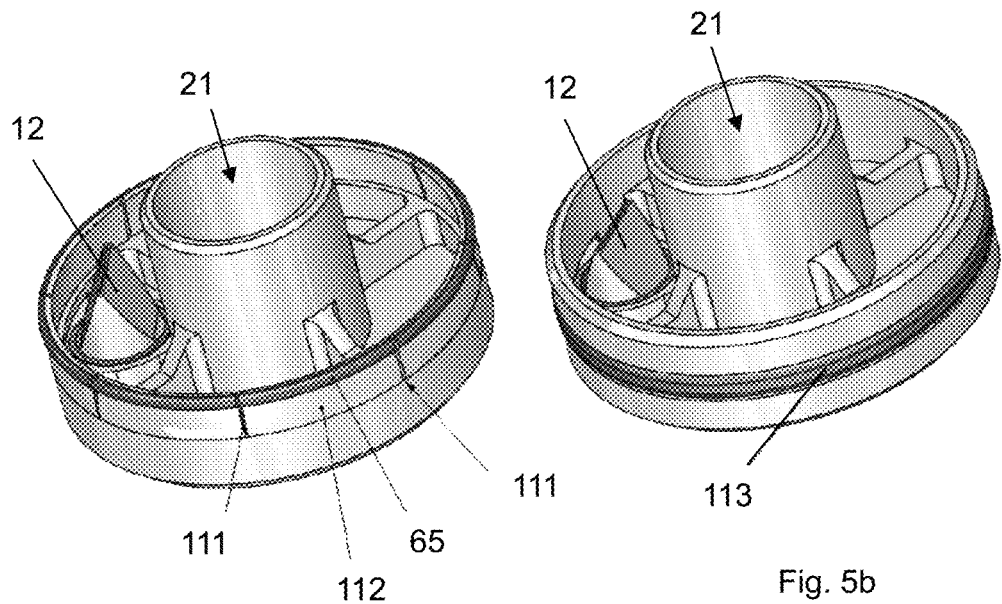
Fig. 5a
Fig. 5b
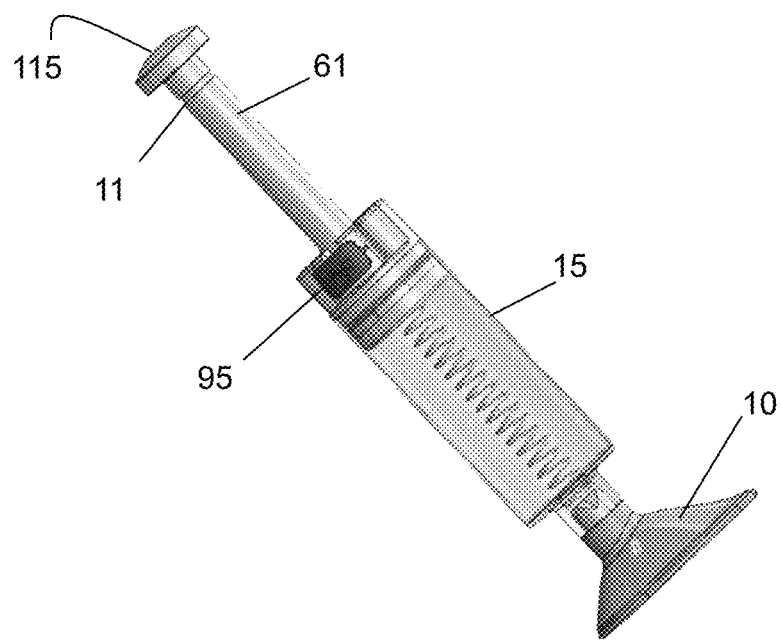
Fig. 6

AUTOMATED AIRWAY OBSTRUCTION CLEARANCE/DROWNING RESCUE DEVICE AND METHOD OF MAKING AND USING THE SAME

FIELD OF THE INVENTION

The presently disclosed subject matter is directed to an automated airway obstruction clearance and drowning rescue device and to methods of making and using the disclosed device.

BACKGROUND OF THE INVENTION

Choking on food and/or small objects remains one of the most gruesome and potentially fatal occurrences that can happen to infants, children, and adults. According to the New York State Department of Health, choking is the fourth leading cause of unintentional death in children under the age of five and at least one child dies from choking on food every five days in the U.S. Adults, particularly older adults, also have a high risk for choking. FIG. 1 from the CDC/NCHS/National vital Statistics System 2007-2010 represents both the pediatric and adult incidence of choking on food as the underlying cause of death.

Choking is defined as a condition that occurs when breathing is impeded by a blockage inside the respiratory tract. If not cleared by spontaneous coughing or other actions, intervention by others may be required to remove the object causing choking. It has become a recommended practice in emergency medical circles to employ the Heimlich maneuver, in which a second person suddenly squeezes the victim's torso below from behind the body and beneath the rib cage. The Heimlich maneuver creates pressure in the lungs intended to expel the object. However, the Heimlich maneuver is not always successful. For example, it is possible that the victim cannot be moved into a position enabling proper application of the Heimlich maneuver. Further, the Heimlich maneuver is not effective if the victim lacks sufficient air in the lungs to develop enough pressure to expel the object. This could arise from having ingested the object immediately upon completing an exhaling step in the breathing cycle, or from having exhaled air by coughing.

In these situations, placing a source of suction to the mouth of the victim has proven to be effective. To this end, vacuum pumps have been used in the prior art in an effort to dislodge items from a choking victim's throat. However, an effective aspiration vacuum needed to dislodge an obstruction is dependent on the device volume, actuation force, and speed of aspiration. As a result, successful use of prior art devices is dependent on the dexterity, strength, and state of mind of the operator. Without optimal physical and mental state of the operator, prior art aspiration vacuums may not be sufficient to clear the airway and/or may require multiple applications. In addition, due to misuse, many prior art vacuum pumps build up pressure slowly and gradually and therefore do not provide an instantaneous vacuum surge for maximum effectiveness.

Every year in the United States there are an estimated 4,000 fatal drownings and 8,000 non-fatal drownings. The first step in this type of rescue is immediate provision of ventilation. It would be beneficial to provide a device configured to extract water from the airway, bronchi, and lungs of a drowning victim to facilitate effective ventilation.

It would therefore be beneficial to provide an automated aspiration device that overcomes the shortcomings of the prior art, providing applications in both airway obstruction clearance and drowning rescue.

SUMMARY OF THE INVENTION

The disclosed subject matter is directed to an aspiration device. Specifically, the device can be optionally fitted with a facemask defined by a cup and a hollow neck in fluid communication with the cup, wherein the cup is sized and shaped to fit over a user's nose and mouth. The device includes a cylinder defined by a hollow interior and opposed first and second ends. The device further includes a one-way check valve positioned between the cylinder first end and the facemask neck. The check valve prevents air from entering the victim's mouth when the piston is pushed down. The device comprises an activation spring positioned within the cylinder interior at the first end, wherein the activation spring is convertible between a first, compressed position and a second, extended position. The device comprises a piston positioned within the cylinder interior, configured to travel between the first and second ends of the cylinder. The piston divides the cylinder interior into a first chamber that includes the activation spring and a second chamber that includes a piston rod. The piston rod comprises a face that directly contacts the activation spring, wherein the piston is configured to travel between the first and second ends of the cylinder. The device includes an endcap permanently attached and/or positioned at the second end of the cylinder, the endcap defined by a central aperture an aspiration button (e.g., spring-loaded aspiration button). The aspiration button comprises a front face, an opposed rear wall, and a central slot with a first region having a first diameter and a second locking region having a diameter less than the first diameter. The piston rod is attached to the piston at a first rod end, with a length that extends through the endcap aperture. The piston rod includes a second rod end fitted as a knob, wherein the piston rod includes a detent groove adjacent to the second end. The aspiration button includes a first locked position where the button engages the detent groove on the piston rod, wherein the piston cannot advance towards the cylinder second end, and when the button is pushed inward it disengages the detent groove allowing the piston rod to move freely in the cap aperture. The spring-loaded aspiration button also includes a second aspiration position that allows the piston to advance towards the cylinder second end via spring force, thereby creating a vacuum in the first chamber. Thus, the aspiration button includes a first locked position wherein the piston cannot advance towards the cylinder second end, and a second aspiration position wherein the piston advances towards the cylinder second end, thereby creating a vacuum in the first chamber.

In some embodiments, the piston comprises a lip seal about a circumference of the piston.

In some embodiments, the piston includes an outer O-ring.

In some embodiments, the piston comprises a check valve.

In some embodiments, the second aspiration position is characterized by aligning the slot first region on the aspiration button with the piston rod by pushing the aspiration button in.

In some embodiments, the aspiration button is held in place (e.g., the locked position) by a button spring.

In some embodiments, the piston rod second end comprises a knob.

In some embodiments, the end cap aperture has the same diameter as the aspiration button slot first region.

In some embodiments, the facemask is disposable.

In some embodiments, the device is automated and configured for single-handed device by a user.

In some embodiments, the presently disclosed subject matter is directed to a method of removing an object from an airway of a user. Particularly, the method comprises positioning the button of the disclosed aspiration device in the first locked position. The method includes positioning the facemask over the mouth and nose of the user. The method includes activating the aspiration button inward to the second position (e.g., an aspirate position), thereby allowing the piston to move toward the second cylinder end in response to extension of the activation spring, whereby a vacuum is created in the first chamber. The vacuum is conducted through the facemask to remove an object from the airway of the user.

In some embodiments, the user is a choking victim.

In some embodiments, the aspiration device is reloaded by advancing the piston rod and piston toward the first end of the cylinder, aligning the piston rod detent groove with the aspiration button allowing the spring-loaded aspiration button to slide into the locked position, thereby compressing the activation spring.

In some embodiments, the presently disclosed subject matter is directed to a method of removing water from the lungs of a drowning victim. Particularly, the method comprises positioning the button of the disclosed aspiration device in the first locked position. The method includes positioning a facemask over the mouth and nose of the drowning victim. The method includes activating the button inward to an aspirate position, thereby allowing the piston to move toward the second cylinder end in response to extension of the activation spring, whereby a vacuum is created in the first chamber. The vacuum is conducted through the facemask to remove water from the lungs of a drowning victim.

In some embodiments, the aspiration button is held in locked position by a button spring and friction.

BRIEF DESCRIPTION OF THE DRAWINGS

FIG. 3c is a side plan view of a device cylinder in accordance with some embodiments of the presently disclosed subject matter.

FIG. 3d is a cross-sectional view of a device cylinder in accordance with some embodiments of the presently disclosed subject matter.

FIG. 4a is a side plan view of a device cylinder cap in accordance with some embodiments of the presently disclosed subject matter.

FIG. 4b is a perspective view of a device aspirate button in accordance with some embodiments of the presently disclosed subject matter.

FIGS. 5a and 5b are bottom perspective views of device end caps in accordance with some embodiments of the presently disclosed subject matter.

FIG. 6 is a perspective view of an aspiration device in accordance with some embodiments of the presently disclosed subject matter.

DETAILED DESCRIPTION OF THE INVENTION

Figure 1:
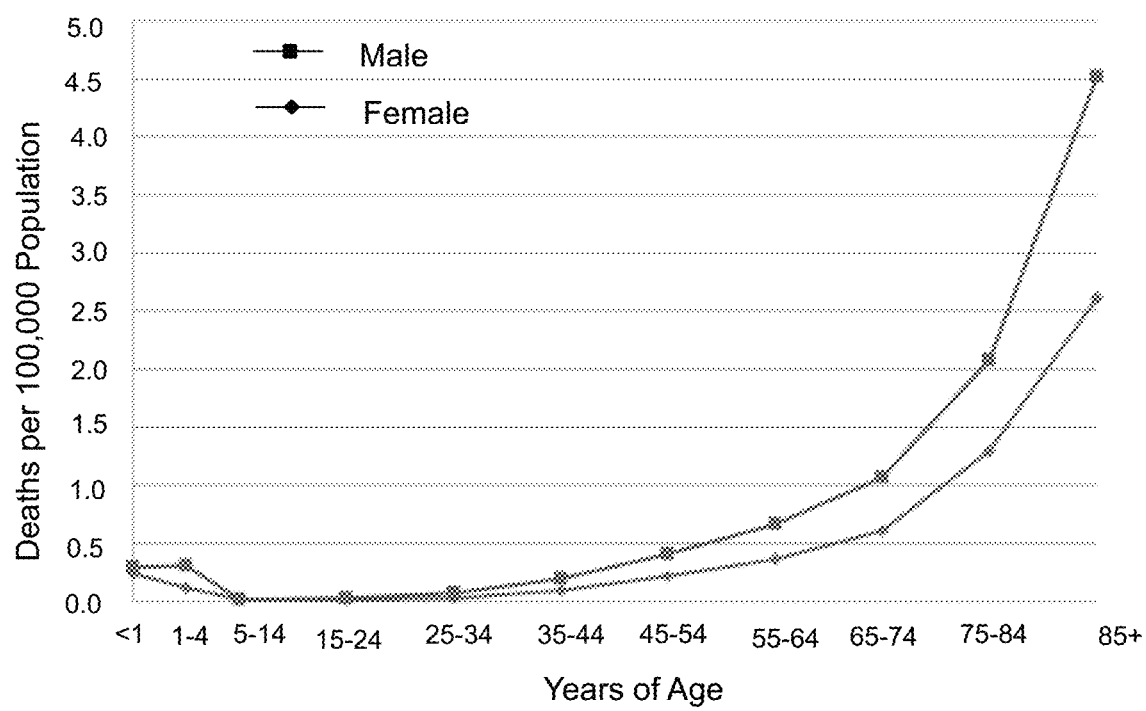
FIG. 1 is a graph depicting the deaths due to choking versus age provided by CDC/NCHS/National vital Statistics System 2007-2010.

For the purpose of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e., at least one) of the grammatical object of the article. By way of example, "an element" means at least one element and can include more than one element. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise indicated, all numbers expressing quantities of components, conditions, and so forth used in the specification and claims are to be understood as being modified in all instances by the term "about." Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods. Thus, the term "about" is used to provide flexibility to a numerical range endpoint by providing that a given value may be "slightly above" or "slightly below" the endpoint without affecting the desired result.

As used herein, the term "and/or" includes any and all combinations of one or more of the associated listed items.

Relative terms such as "below" or "above" or "upper" or "lower" or "horizontal" or "vertical" may be used herein to describe a relationship of one element, layer, or region to another element, layer, or region as illustrated in the drawing figures. It will be understood that these terms and those discussed above are intended to encompass different orientations of the device in addition to the orientation depicted in the drawing figures.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

All methods described herein can be performed in any suitable order unless otherwise indicated herein or otherwise clearly contradicted by context. The use of any and all examples, or exemplary language (e.g., "such as") provided herein, is intended merely to better illuminate the invention, and does not pose a limitation on the scope of the invention unless otherwise claimed. No language in the specification should be construed as indicating any unclaimed element as essential to the practice of the invention.

Unless otherwise defined, all technical terms used herein have the same meaning as commonly understood by one of ordinary skill in the art to which this disclosure belongs.

Figure 2:
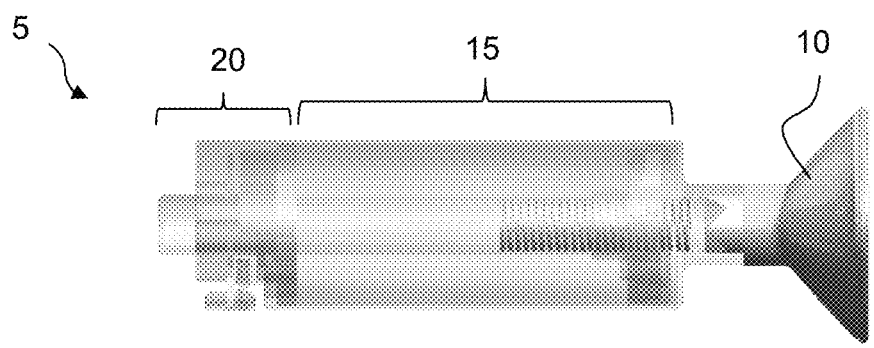
FIG. 2 is a side plan view of an aspiration device in accordance with some embodiments of the presently disclosed subject matter.

As shown in FIG. 2, the presently disclosed subject matter is directed to an aspiration device 5 that can be used to dislodge an object from a choking victim's airway and/or to remove water from a drowning victim's lungs. The term "aspiration device" refers to an assembly that can effectively be used to dislodge an object (e.g., food) from a choking victim's airway and/or water from a drowning victim's lungs. The disclosed device includes hollow cylinder 15 comprising a movable piston mounted within the cylinder interior. A system for automatically moving the piston rearwardly to increase the size of cylinder chamber volume one is provided. The aspiration device will be fitted with facemask 10 that can be positioned against the face of the choking victim and provides a seal around the victim's mouth and nose. An airway extends between the cylinder chamber and the facemask so that air or water can be drawn into the cylinder chamber through the mask when the piston is moved in a rearward direction. As discussed in detail below, a compressed spring disposed within the cylinder chamber biases the piston in a rearward direction. The spring can be tailored to meet suction requirements of users including drowning/choking victims. A releasable latch that allows the piston to move from a forward locked position to a released position is housed within endcap 20.

As noted above, aspiration device 5 includes facemask 10 configured to fit around a user's nose and mouth. The facemask can be of conventional and known construction, including a flexible and rounded cup that is placed over and conforms to a person's mouth and nose to exclude air flow communication between the person's air passages and the ambient atmosphere. The facemask can also include a hollow neck in fluid communication with the cup. Facemask 10 therefore connects the breathing passages of the victim to a vacuum generated within device 5 and prevents excessive leakage at the victim's face that would defeat effectiveness of the device. With the mouth and nose area of the victim housed within the facemask cup interior, ambient air is prevented from relieving the vacuum within the facemask. Vacuum will therefore remove foreign objects that may have become lodged within the victim's throat or water from the lungs of a drowning victim, as explained in detail below. The term "victim" therefore can include persons that are choking on foreign objects (e.g., food) and persons that are being rescued from drowning.

The outer edge of the facemask cup can include a ring that is in direct contact with the user's skin during use. In addition to providing comfort to the user, the ring prevents the vacuum generated by device 5 from being countered by a rush of air in proximity to the victim's mouth. The ring can be constructed from rubber, plastic, or any other suitable material.

Any of the wide variety of commercially available facemasks can be used. For example, a commercially available CPR mask kit that includes masks for adults, children, and infants can be supplied with device 5. The appropriate mask can be fitted on the device using any method, such as a taper fit.

The term "check valve" refers to any one-way valve that resists or prevents reverse air flow through the device, back into the facemask. Thus, the check valve ensures that when in use, device 5 enables the flow of air or water unidirectionally, from the user's airway or lungs, through the facemask, through check valve 45, and into cylinder 15. The check valve thus prevents air or water from passing through facemask 10 from the cylinder chamber and into a victim's mouth.

Optionally an elastic strap or other retention element (not shown) can be attached to the facemask for extending around the victim's head to secure the mask to the victim.

Facemask 10 can be constructed from any suitable material. For example, the facemask can be constructed from a soft deformable plastic material to prevent injury to a victim during use, but with a material that has sufficient rigidity so that it will not collapse when suction force is applied.

The facemask can be configured in a variety of sizes (e.g., adult, medium, or infant sizes).

In some embodiments, facemask 10 is disposable, thereby minimizing the sanitation requirements and the transmission of diseases between users. However, in other embodiments, the facemask can be cleaned and reused multiple times.

Figure 3A:
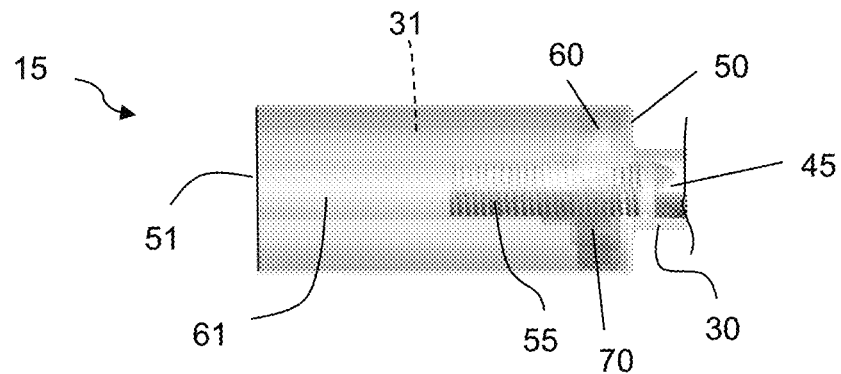
FIG. 3a is a side plan view of a device cylinder in accordance with some embodiments of the presently disclosed subject matter.
Figure 3B:
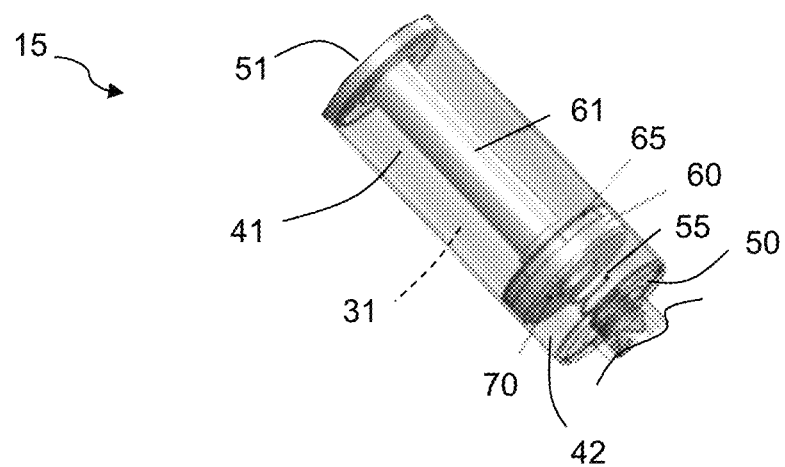
FIG. 3b is a perspective view of a device cylinder in accordance with some embodiments of the presently disclosed subject matter.

Aspiration device 5 also includes cylinder 15 with interior 31 that houses the components for generating a vacuum. As shown in FIGS. 3a and 3b, the cylinder includes first and second ends 50, 51. First end 50 includes tapered neck 30 that houses check valve 45. Second end 51 is in direct contact with cap 20.

The interior of cylinder 15 includes an activation spring 55 positioned at first end 50. The term "spring" refers any resilient or elastic body, device, or combination of bodies or devices capable of storing and releasing mechanical energy. Spring 55 is compressed between first end 50 of the cylinder and a bore positioned in the piston rod. Piston 60 is thus connected to piston rod 61 that extends through the end cap, as discussed below.

Spring 55 urges or biases the piston in a rearward direction (e.g., towards second end 51 of the cylinder). The piston thus divides the cylinder interior into an upper chamber 41 located above the upper side of the piston and a lower chamber 42 located below the lower side of the piston as shown in FIG. 3b. The piston is movable (forwardly and rearwardly) along the length of the cylinder interior. Thus, piston 60 can have an outer diameter slightly less than the inner diameter of the cylinder interior 31. Movement of the piston rearwardly (towards cylinder second end 51) expands the volume of the lower chamber, thereby increasing the vacuum therein. Movement of the piston forwardly (towards cylinder first end 50) reduces the volume of the lower chamber. Check valve 70 located in the piston allows air to escape, ensuring there is no increase in pressure as the piston moves towards the first end 50 of the cylinder.

The piston can be shaped to correspond to the interior shape of cylinder. Further, the size of piston 60 can be such that it is slidable within cylinder interior using a very close clearance fit (e.g., such that it is leak-resistant between chambers 41, 42). Alternatively, the piston include lip seal 65 about the piston circumference to ensure a good fit. Alternatively, a flexible O-ring can be adapted for use with the piston to provide fluid leak resistance.

Cylinder 15 can be configured in any suitable dimensions. For example, the cylinder can have length 75 of about 3-10 inches. The term "length" refers to the longest-straight line distance between first and second ends 50, 51 of the cylinder, as shown in FIG. 3c. The cylinder can further include diameter 80 of about 1-5 inches, as shown in FIG. 3d. The term "diameter" refers to the longest straight line distance that passes through the center of the cylinder.

Figure 4C:
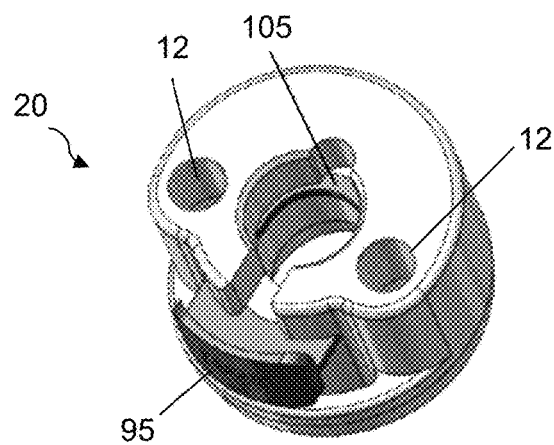
FIGS. 4c and 4d are perspective views of device end caps in accordance with some embodiments of the presently disclosed subject matter.

As noted above, device 5 also includes cylinder cap 20, as illustrated in FIG. 4a. As shown, the cylinder cap includes central aperture 21 through which piston rod 61 passes. A knob 115 is adhered to the end of piston rod 61, allowing a user an element upon which to push on readying the device for use. The end cap also includes aspiration button 90 that effectively cocks and triggers the device. As illustrated in FIG. 4b, the button includes front wall 95 that a user can press to maneuver the button from a first, cocked position to a second aspirate position. The button also includes keyhole slot 100 that is positioned within the cap such that it aligns with central aperture 21. As illustrated, the keyhole slot includes first region 101 and second region 102. The first region has a larger diameter compared to the second region. The entire periphery of second region 102 engages a circumferential piston rod detent groove 11 in a first, locked position. In the locked configuration of FIG. 4c, the second (e.g., smaller) region of the keyhole slot is configured within aperture 21 such that the entire periphery of the second region 102 engages the piston detent groove and prevents the piston rod from sliding to activate the device. In the locked position, the button is held in place by the force of button spring 110 and friction.

Figure 4D:
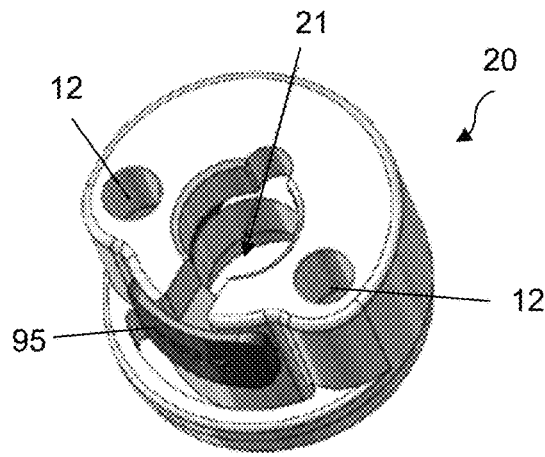

In the second position illustrated in FIG. 4d, the piston rod is free to slide within the cap aperture because outer wall 105 and periphery of keyhole slot 102 are not present within aperture 21, thus disengaging the piston rod detent groove. In these embodiments, the front wall of the button is flush against the cap and the keyhole slot is fully aligned with the central aperture.

Figure 4E:
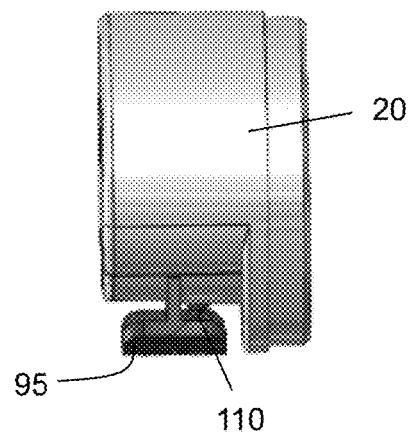
FIG. 4e is a side plan view of a device end cap in accordance with some embodiments of the presently disclosed subject matter.

Button 90 is spring loaded, such that spring 110 enables the button to slide into the piston rod detent groove when it is aligned with the button slide in the locked position, as shown in FIG. 4e. At this point, the piston rod is locked in position and is not free to slide through the end cap. Once pushed in, the button is held in this position by the larger keyhole diameter and OD of the piston rod, the piston rod is free to slide through the end cap aperture 21. Once the button is pushed, the user does not need to hold the button in.

FIGS. 5a and 5b depict a bottom view of piston 60, illustrating a lip seal finger configuration and an O-ring 113 sealing configuration, respectively. Particularly, FIG. 5a illustrates an end cap with a lip seal finger configuration. The term "lip seal" refers to ring-shaped elastomeric seal designed for use around a shaft or inside a cylinder, characterized by the presence of lip finger 112 positioned between slots 111. The lip seal seals the mating surface inside the cylinder.

The end cap also includes one or more vent holes 12, that allow air to escape chamber 41, when the piston advances towards the end cap. The cap can include any number of vent holes.

Knob 115 can be positioned on piston rod 61 to enable a user to push down more easily while cocking the device, as shown in FIG. 6. The term "knob" broadly includes any element that can be pushed by a user.

Figure 7A:
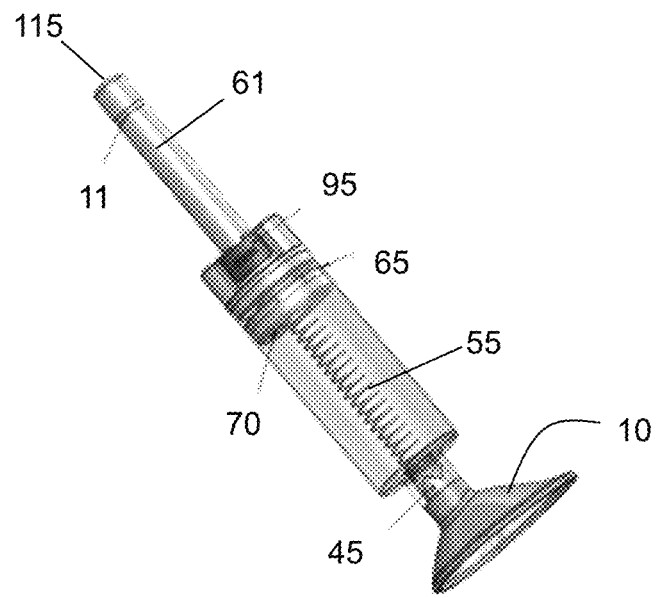
FIGS. 7a-7c are perspective views of a method of using an aspiration device in accordance with some embodiments of the presently disclosed subject matter.
Figure 7B:
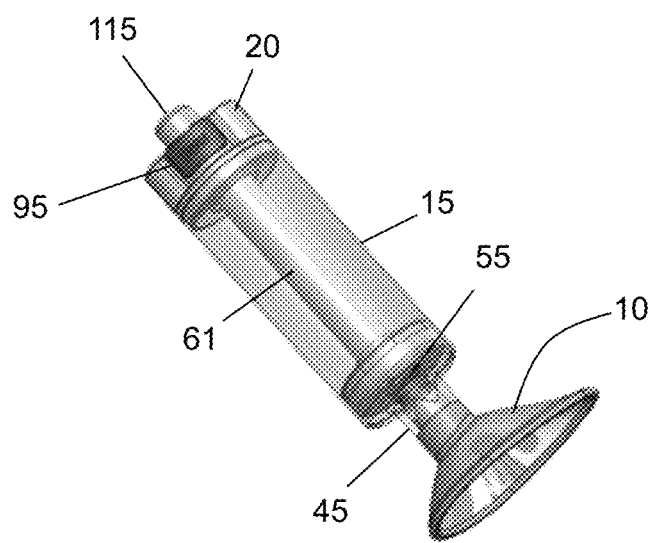
Figure 7C:
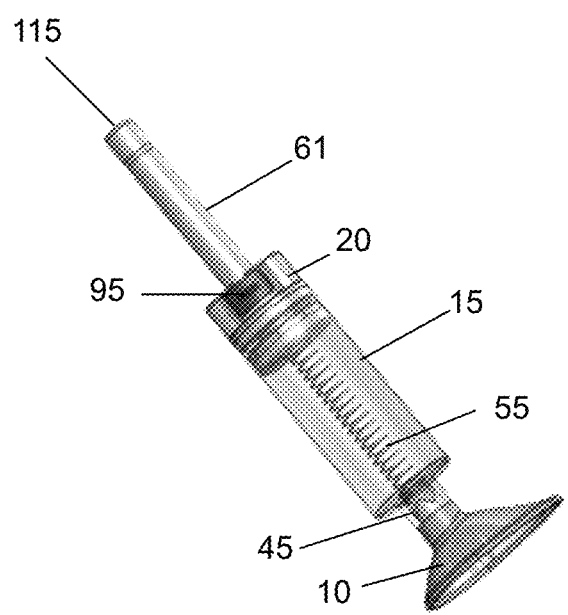

FIGS. 7a and 7b illustrates one embodiment of use and storage configurations of device 5. As shown in the figures, piston rod 61 is fully extended through cap 20. As the piston rod is pushed in a downward direction (e.g., towards the cylinder), aspiration spring 55 compresses. In addition, the aspiration check valve 45 closes and the de-airing check valve opens, thereby allowing air in the cylinder to escape and exit through the vent hole in the cap. When the detent groove on the piston rod aligns with the slot in spring-loaded aspiration button 95, the aspiration button moves out and the piston assembly is locked in position of FIG. 7a. The facemask can then be placed over the nose and mouth of the victim. The user can then push button 95 to initiate aspiration. Specifically, when the button is pushed, aspiration spring 55 expands, the de-airing check valve closes and the aspiration check valve 45 opens, allowing airway suction and removal of the airway obstruction or water from a drowning victim's lungs. A vacuum is generated within chamber 42 when piston 60 is rapidly forced towards second end 51 of the cylinder due to expansion of spring 55, as shown in FIG. 7c. Conducted through facemask 10, vacuum thus effectively acts on the choking or drowning victim. The device can be re-cocked and reused if necessary.

It should be appreciated that the spring force can be customized with respect to different patient populations. For example, the spring force needed to dislodge an item from an adult's airway may not be suitable for use with a child.

As described in detail herein, device 5 can be used to remove an object from a user's airway. However, the device is capable of having many different uses. For example, the device can be used to help remove water from the lungs of a drowning victim.

The disclosed device offers many benefits over prior art aspiration devices. Particularly, device 5 enables single-handed operation by a user since it is activated by simply pushing a button. To this end, the device can be easily deployed without the use of the user's second hand and/or help from a second person.

Advantageously, a person can self-administer device 5 in the absence of others who could otherwise assist.

Device 5 is portable and can be carried to emergency sites by emergency personnel.

Device 5 is easy to use with the simple push of a button, as discussed in detail herein above. As such, even children or the elderly can use device 5.

The disclosed device can be reused multiple times by pushing piston rod knob 115 down to the loaded position and pushing activation button 95 when needed.

Device 5 does not require manual aspiration by a user. Rather, the device is automated and only requires the activation of a single button for use. As a result, successful deployment of the device is not dependent on the user's state of mind and/or mental anxiety in a choking or other emergency situation.

Advantageously, device 5 does not require extensive user training, strength, or physical dexterity to be used. Any of a wide variety of users can successfully use the disclosed aspiration device.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the invention. In this regard, for example, different combinations of elements and/or functions than those explicitly described above are also contemplated within the scope of the invention. Although specific terms are employed herein, they are used in a generic and descriptive sense only and not for purposes of limitation.

What is claimed is:

1. An aspiration device comprising:
   a cylinder defined by a hollow interior and opposed first and second ends; a one-way check valve positioned between the cylinder first end and a facemask neck;
   an activation spring positioned within the cylinder interior at the first end, wherein the activation spring is convertible between a first, compressed position and a second, extended position;
   a piston positioned within the cylinder interior, the piston comprising a face that directly contacts the activation spring, wherein the piston is configured to travel between the first and second ends of the cylinder; and wherein the piston divides the cylinder interior into a first chamber that includes the activation spring and a second chamber that includes a piston rod;
   an endcap positioned at the second end of the cylinder, the endcap defined by a central aperture and an aspiration button;
   wherein the aspiration button comprises a front face, an opposed rear wall, and a central slot with a first region having a first diameter and a second region having a diameter less than the first diameter and positioned adjacent to the rear wall;
   wherein the piston rod is attached to the piston at a first rod end, with a length that extends through the endcap aperture, and a second rod end fitted with a knob, wherein the piston rod includes a detent groove adjacent to the second rod end;
   wherein the aspiration button is configured to be located in a first locked position wherein the piston cannot advance towards the cylinder second end, and a second aspiration position wherein the piston advances towards the cylinder second end, thereby creating a vacuum in the first chamber.

2. The aspiration device of claim 1, further comprising a facemask defined by a cup and the facemask neck in fluid communication with the cup, wherein the cup is sized and shaped to fit over a user's nose and mouth.

3. The aspiration device of claim 1, wherein the piston comprises a lip seal about a circumference of the piston.

4. The aspiration device of claim 1, wherein the piston includes an outer O-ring.

5. The aspiration device of claim 1, wherein the piston comprises a check valve.

6. The aspiration device of claim 1, wherein the second aspiration position is characterized by aligning the slot first region on the aspiration button with the piston rod by pushing the aspiration button in.

7. The aspiration device of claim 1, wherein the aspiration button is held in the locked position by a button spring.

8. The aspiration device of claim 1, wherein the end cap aperture has the same diameter as the aspiration button slot first region.

9. The aspiration device of claim 1, wherein the device is automated and configured for single-handed use by a user.

10. A method of removing an object from an airway of a user, the method comprising:
    positioning the aspiration button of the aspiration device of claim 1 in the first locked position;
    positioning a facemask over the mouth and nose of the user;
    positioning the aspiration button in the second aspiration position, thereby allowing the piston to move toward the second cylinder end in response to extension of the activation spring;
    whereby a vacuum is created in the first chamber;
    wherein the vacuum is conducted through the facemask to remove an object from the airway of the user.

11. The method of claim 10, wherein the user is a choking victim.

12. The method of claim 10, wherein the aspiration device is reloaded by advancing the piston rod and piston toward the first end of the cylinder, aligning the piston rod detent groove with the aspiration button allowing the aspiration button to slide into the locked position, thereby compressing the activation spring.

13. A method of removing a water from an airway of a drowning victim, the method comprising:
    positioning the aspiration button of the aspiration device of claim 1 in the first locked position;
    positioning a facemask over the mouth and nose of the drowning victim;
    positioning the aspiration button in the second aspiration position, thereby allowing the piston to move toward the second cylinder end in response to extension of the activation spring;
    whereby a vacuum is created in the first chamber;
    wherein the vacuum is conducted through the facemask to remove water from the airway of the drowning victim.

14. The method of claim 13, wherein the aspiration device is reloaded by advancing the piston rod and piston toward the first end of the cylinder, aligning the piston rod detent groove with the aspiration button allowing the aspiration button to slide into the locked position, thereby compressing the activation spring.

15. The method of claim 13, wherein the piston comprises a lip seal about a circumference of the piston.

16. The method of claim 13, wherein the piston comprises a check valve.

17. The method of claim 13, wherein the aspiration button is held in locked position by a button spring and friction.

18. The method of claim 13, wherein the aspiration button is spring-loaded.

* * * * *